US008147810B2

(12) United States Patent
Pan et al.

(10) Patent No.: US 8,147,810 B2
(45) Date of Patent: Apr. 3, 2012

(54) METHOD OF MAKING AN ANTIPERSPIRANT ACTIVE COMPOSITION HAVING SEC CHROMATOGRAM EXHIBITING HIGH SEC PEAK 4 INTENSITY

(75) Inventors: Long Pan, Cherry Hill, NJ (US); LaTonya Kilpatrick-Liverman, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 263 days.

(21) Appl. No.: 12/531,145

(22) PCT Filed: Aug. 6, 2009

(86) PCT No.: PCT/US2009/052906
§ 371 (c)(1),
(2), (4) Date: Sep. 14, 2009

(87) PCT Pub. No.: WO2011/016807
PCT Pub. Date: Feb. 10, 2011

(65) Prior Publication Data
US 2011/0182841 A1    Jul. 28, 2011

(51) Int. Cl.
*A61K 8/28* (2006.01)
*A61K 8/26* (2006.01)
*A61Q 15/00* (2006.01)

(52) U.S. Cl. .............................. 424/66; 424/68
(58) Field of Classification Search .................. None
See application file for complete search history.

(56) References Cited

U.S. PATENT DOCUMENTS

| | | | |
|---|---|---|---|
| 3,979,510 A * | 9/1976 | Rubino | 424/47 |
| 3,991,176 A * | 11/1976 | Rubino | 424/47 |
| 4,871,525 A | 10/1989 | Giovanniello et al. | |
| 4,900,534 A | 2/1990 | Inward | |
| 5,330,751 A | 7/1994 | Curtin et al. | |
| 5,348,720 A | 9/1994 | Vincenti et al. | |
| 5,358,694 A | 10/1994 | Giovanniello | |
| 5,643,558 A | 7/1997 | Provencal et al. | |
| 5,705,171 A | 1/1998 | Iovanni et al. | |
| 5,997,850 A | 12/1999 | Tang et al. | |
| 6,010,688 A | 1/2000 | Shen | |
| 6,066,314 A | 5/2000 | Tang et al. | |
| 6,074,632 A | 6/2000 | Shen | |
| 6,136,302 A | 10/2000 | Juneja et al. | |
| 6,149,897 A | 11/2000 | Swaile | |
| 6,245,325 B1 | 6/2001 | Shen | |
| 6,342,210 B1 | 1/2002 | Cai et al. | |
| 6,375,937 B1 | 4/2002 | Chopra et al. | |
| 6,436,381 B1 | 8/2002 | Carrillo et al. | |
| 6,726,901 B2 | 4/2004 | Yin et al. | |
| 6,835,373 B2 | 12/2004 | Kolodzik et al. | |
| 6,902,724 B1 | 6/2005 | Parekh et al. | |
| 6,936,242 B2 | 8/2005 | Elliot et al. | |
| 6,942,850 B2 | 9/2005 | Coe et al. | |
| 6,969,510 B2 | 11/2005 | Holerca et al. | |
| 7,105,691 B2 | 9/2006 | Holerca et al. | |
| 7,189,387 B2 | 3/2007 | Chuah et al. | |
| 7,229,611 B2 | 6/2007 | Zamudio-Tena et al. | |
| 7,256,875 B2 | 8/2007 | Maier et al. | |
| 2004/0265255 A1 | 12/2004 | Holerca et al. | |
| 2005/0265939 A1 | 12/2005 | Li | |
| 2006/0153788 A1 | 7/2006 | Swaile et al. | |
| 2006/0204463 A1 * | 9/2006 | Tang et al. | 424/66 |
| 2006/0292098 A1 | 12/2006 | Scavone et al. | |
| 2007/0003499 A1 | 1/2007 | Shen et al. | |
| 2007/0020211 A1 * | 1/2007 | Li et al. | 424/68 |
| 2007/0110687 A1 | 5/2007 | Mattai et al. | |
| 2007/0196302 A1 | 8/2007 | Pratt et al. | |
| 2007/0196303 A1 | 8/2007 | Li et al. | |

FOREIGN PATENT DOCUMENTS

| | | |
|---|---|---|
| GB | 2144992 | 8/1984 |
| WO | WO 2006/103092 | 10/2006 |
| WO | WO 2009075678 A1 * | 6/2009 |
| WO | WO 2009076591 A1 * | 6/2009 |

OTHER PUBLICATIONS

Bottero, The Journal of Physical Chemistry, 84, 1980.*
U.S. Appl. No. 12/446,045, filed Apr. 17, 2009.
Allouche et al., 2000, "$Al_{30}$: A Giant Aluminum Polycation," Agnew. Chem. Int. Ed. 39(3):511-514.
Chen et al., 2006, "Evaluation of $Al_{30}$ Polynuclear Species in Polyaluminum Solutions As Coagulant for Water Treatment," Chemosphere 64(6):912-918.
Chen et al., 2009, "On the Acid-Base Stability of Keggin $Al_{13}$ and $Al_{30}$ Polymers in Polyaluminum Coagulants," J. Mater. Sci, 44:3098-3111.
Huang et al., 2006, "Separation and Purification of Nano-$Al_{13}$ by UF Method," Colloids and Surfaces A: Physicochem. Eng. Aspects 275:200-208.
Shen, 1998, "Synthesis and Speciation of Polyaluminum Chloride for Water Treatment," Environment International 24(8):899-910.
Zhang et al., 2008, "Coagulation Characteristics of Polyaluminum Chlorides PAC-$Al_{30}$ on Humic Acid Removal from Water," Separation and Purification Technology 63:642-647.

(Continued)

*Primary Examiner* — Robert A Wax
*Assistant Examiner* — William Craigo
(74) *Attorney, Agent, or Firm* — Michael F. Morgan

(57) ABSTRACT

A method of making the antiperspirant active compositions having SEC chromatogram exhibiting high SEC peak 4 intensity, which are described in PCT/US2007/087145 (Published as WO2009/075678) and PCT/US2008/086556 (Published as WO2009/076591). The method uses a combination of sodium hydroxide with a source of calcium ions.

22 Claims, No Drawings

OTHER PUBLICATIONS

Allouche et al., 2003, "Conversion of $Al_{13}$ Keggin ε into $Al_{30}$: A Reaction Controlled by Aluminum Monomers," Inorganic Chemistry Communications 6:1167-1170.

Casey, 2005, "Large Aqueous Aluminum Hydroxide Molecules," Chemical Reviews 106(1):1-16.

Chen et al., 2007, "Effect of Thermal Treatment on the Formation and Transformation of Keggin $Al_{13}$ and $Al_{30}$ Species in Hydrolytic Polymeric Aluminum Solutions," Colloids and Surfaces A: Physicochem. Eng. Aspects 292:110-118.

Fu et al., 1991, "Aging Processes of Alumina Sol-Gels: Characterization of New Aluminum Polyoxycations by $^{27}Al$ NMR Spectroscopy," Chem. Mater. 3:602-610.

International Search Report and Written Opinion in International Application No. PCT/US07/087145 mailed Apr. 6, 2007.

International Search Report and Written Opinion in International Application No. PCT/US08/086556 mailed Apr. 6, 2009.

Roswell et al., 2000, "Speciation and Thermal Transformation in Alumina Sols: Structures of the Polyhydroxyoxoaliminum Cluster $[AL_{30}O_8(OH)_{56}(H_2O)_{26}]^{18+}$ and Its δ-Keggin Moieté," J. Am. Chem. Soc. 122:3777-3778.

Shafran et al., 2005, "The Static Anion Exchange Method for Generation of High Purity Aluminum Polyoxocations and Monodisperse Aluminum Hydroxide Nanoparticles," J. Materials Chemistry 15:3415-3423.

File History of U.S. Appl. No. 12/446,045 to Oct. 20, 2011.

\* cited by examiner

METHOD OF MAKING AN ANTIPERSPIRANT ACTIVE COMPOSITION HAVING SEC CHROMATOGRAM EXHIBITING HIGH SEC PEAK 4 INTENSITY

BACKGROUND OF THE INVENTION

Antiperspirant salts, such as aluminum chlorohydrex (also called aluminum chlorohydrex polymeric salts and abbreviated here as "ACH") and aluminum zirconium glycine salts (abbreviated here as "ZAG". "ZAG complexes" or "AZG"), are known to contain a variety of polymeric and oligomeric species with molecular weights (MW) of 100-500,000. It has been clinically shown that, in general, the smaller the species, the higher the efficacy for reducing sweat.

In an attempt to increase the quality and quantity of smaller aluminum and/or zirconium species, a number of efforts have focused on: (1) how to select the components of ACH and ZAG that affect the performance of these materials as antiperspirants; and (2) how to manipulate these components to obtain and/or maintain the presence of smaller types of these components. These attempts have included the development of analytical techniques to identify the components. Size exclusion chromatography ("SEC") or gel permeation chromatography ("GPC") are methods frequently used for obtaining information on polymer distribution in antiperspirant salt solutions. With appropriate chromatographic columns, generally five distinctive groups of polymer species can be detected in commercial ACH and ZAG complexes appearing in a chromatogram as peaks 1, 2, 3, 4 and a peak known as "5,6". Peak 1 is the larger Zr species (greater than 60 Angstroms). Peaks 2 and 3 are larger aluminum species. Peak 4 is smaller aluminum species (aluminum oligomers, or small aluminum cluster) and has been correlated with enhanced efficacy for both Al and Al/Zr salts. Peak 5, 6 is the smallest aluminum species. Various analytical approaches for characterizing the peaks of ACH and various types of ZAG actives are found in "Antiperspirant Actives—Enhanced Efficacy Aluminum-Zirconium-Glycine (AZG) Salts" by Dr. Allan H. Rosenberg (Cosmetics and Toiletries Worldwide, Fondots. D.C. ed., Hartfordshire, UK: Aston Publishing Group, 1993, pages 252, 254-256).

Previously, the inventor has described an antiperspirant active compositions having SEC chromatogram exhibiting high SEC peak 4 intensity in PCT/US2007/087145 (Published as WO2009/075678) and PCT/US2008/086556 (Published as WO2009/076591), both of which are incorporated herein by reference. Described herein is a method of making the antiperspirant.

BRIEF SUMMARY OF THE INVENTION

The present invention provides for a method of making an antiperspirant active composition comprising
I) heating an aqueous solution containing an aluminum salt having an aluminum to chloride molar ratio of about 0.3:1 to about 3:1, optionally with a buffer agent, at a temperature of about 50° C. to about 100° C. to reflux for a period of time of about 1 hour to about 6 hours to obtain an aluminum salt solution;
II) adding an aqueous solution of sodium hydroxide to obtain an aluminum salt solution having an OH:Al molar ratio of about 2:1 to about 2.6:1 to obtain a pH adjusted aluminum salt solution having a pH of about 2 to about 5;
III) providing a calcium ion; and
IV) optionally adding an aqueous solution containing a zirconium compound to the pH adjusted aluminum salt solution to thereby obtain an aluminum-zirconium salt solution having a molar ratio of aluminum to zirconium of about 5:1 to about 10:1.

DETAILED DESCRIPTION OF THE INVENTION

As used throughout, ranges are used as a shorthand for describing each and every value that is within the range. Any value within the range can be selected as the terminus of the range.

The method starts by heating an aqueous solution of an aluminum and chloride containing salt having an aluminum to chloride molar ratio of about 0.3:1 to about 3:1 to a temperature of about 50° C. to about 100° C. In other embodiments, the temperature can be about 75° C. to about 85° C. In another embodiment, the temperature is about 95° C. In one embodiment, the aluminum chloride solution is about 0.01 to about 3M.

Optionally, a buffer can be included in the aqueous solution. Buffers that can be used can be chosen from amino acids, glycine, and betaine. The buffer to aluminum molar ratio in certain embodiments can be about 0.1:1 to about 3:1. In another embodiment, the buffer to aluminum molar ratio is about 0.5:1 to about 2:1. In another embodiment, the buffer to aluminum molar ratio is about 1:1 to about 1.5:1.

The method includes adding sodium hydroxide along with a calcium ion source. The calcium ion can be provided from a base, such as calcium hydroxide or calcium oxide, or from a calcium salt, such as calcium chloride or calcium carbonate.

When the calcium source is a base, it can be added simultaneously with the sodium hydroxide, sequentially before the sodium hydroxide is added, or sequentially after the sodium hydroxide is added For the calcium salt, it can be included in the aluminum salt solution or it can be added after the sodium hydroxide is added.

In one embodiment, when the calcium base is used, the weight ratio of the grams of NaOH/grams $Ca(OH)_2$ can be greater than 0 to about 20. In one embodiment, the ratio is about 1 to about 8. In other embodiments, the ratio is about 1.1, 3.2, 4.9, 5.6, 6.4, or 7.6.

In one embodiment, when the calcium salt is used, the weight ratio of $NaOH/Ca^{2+}$ can be greater than 0 to about 11. In one embodiment the ratio is 1, 2, 3, 4, 5, 6, 7, 8, 9, 10, or 10.8

The compositions may be made in a variety of ways involving a stepwise procedure to neutralize aluminum chloride in solution (optionally buffered) using sodium hydroxide and calcium ion. The procedure generally includes the step of heating an aqueous solution containing an aluminum chloride compound (optionally with a buffer agent) at a temperature of about 50° C. to about 100° C. to reflux for a period of time of about 1 hour to about 5 hours. In one such embodiment, an aqueous solution containing an aluminum chloride compound is heated at a temperature of about 75° C. to about 85° C. to reflux for a period of time of about 3 hours to about 4 hours. In another such embodiment, an aqueous solution containing an aluminum chloride compound and a buffer agent is heated at a temperature of about 75° C. to about 85° C. to reflux for a period of time of about 3 hours to about 4 hours. In one embodiment, the temperature is about 95° C.

In some embodiments, the solution has a buffer agent to aluminum molar ratio of about 0.1:1 to about 3:1. To adjust the pH of the aluminum salt solution, an aqueous solution sodium hydroxide and a calcium ion is added to the heated solution to thereby obtain a pH adjusted aluminum salt solution having a hydroxide to aluminum molar ratio of about 1:1 to about 4:1, and a pH of about 2 to about 5. In one such embodiment, the hydroxide to aluminum molar ratio of about 2:1 to about 3:1. In another such embodiment, the hydroxide to aluminum molar ratio is about 2.1:1 to about 2.6:1.

In some embodiments, a zirconium salt may also be added to the pH adjusted aluminum salt solution. In one other such embodiment, the molar ratio of Al:Zr is about 5:1 to about 10:1. The antiperspirant active composition has a SEC Peak 4 to Peak 3 intensity ratio of at least 7 and a Peak 4 intensity greater than a Peak 5 intensity in aqueous solution.

In one embodiment, an aqueous aluminum chloride salt solution is buffered with betaine monohydrate and held at about 50° C. to about 100° C. to reflux for a period time of about 1 to about 6 hours. To the heated solution, an aqueous solution of sodium hydroxide and calcium ion is added dropwise over a period of time of about 1 to about 3 hours while maintaining the aluminum-betaine solution at about 50° C. to about 100° C. to reflux. In one such embodiment, the solution has a betaine to aluminum molar ratio of about 1.1. In another such embodiment, the solution has a betaine to aluminum molar ratio of about 1.25.

In one embodiment, an aqueous solution containing an aluminum chloride compound is buffered with betaine monohydrate and held at about 75° C. to about 100° C. to reflux for a period of time of about 3 hours to about 4 hours. In another such embodiment, an aqueous solution of sodium hydroxide and calcium is added dropwise over a period of time of about 1 to about 3 hours while maintaining the aluminum-betaine solution at about 75° C. to about 100° C. to reflux. In another embodiment, an aqueous solution of sodium hydroxide and calcium ion is added over a period of time in a series of additions while maintaining the aluminum-betaine solution at about 75° C. to about 100° C. to reflux. In one such embodiment, the inorganic base is added in at least 3 additions. In another such embodiment, the inorganic base is added in at least 5 additions. In another embodiment, a $ZrOCl_2$ solution is added to the pH adjusted aluminum-betaine solution. In one such embodiment, the molar ratio of Al:Zr is about 8. In another such embodiment, the molar ratio of Al:Zr is about 7. In one other such embodiment, the molar ratio of Al:Zr is about 9.

In another embodiment, an aqueous aluminum chloride solution is buffered with glycine and held at about 50° C. to about 100° C. to reflux for a period time of about 1 to about 6 hours. To the heated solution, an aqueous solution of sodium hydroxide and calcium ion is added dropwise over a period of time of about 1 to about 3 hours while maintaining the aluminum-glycine solution at about 50° C. to about 100° C. to reflux. In one such embodiment, the solution has an aluminum to glycine molar ratio of about 0.4. In another such embodiment, the solution has an aluminum to glycine molar ratio of about 0.8.

In another embodiment, an aqueous solution containing an aluminum chloride compound is buffered with glycine and held at about 75° C. to about 100° C. to reflux for a period of time of about 3 hours to about 4 hours. In another such embodiment, an aqueous solution of sodium hydroxide and calcium ion is added dropwise over a period of time of about 1 to about 3 hours while maintaining the aluminum-glycine solution at about 75° C. to about 100° C. to reflux. In another embodiment, an aqueous solution of sodium hydroxide and calcium ion is added over a period of time in a series of additions while maintaining the aluminum-glycine solution at about 75° C. to about 100° C. to reflux. In one such embodiment, the inorganic base is added in at least 3 additions. In another such embodiment, the inorganic base is added in at least 5 additions. In one embodiment, the inorganic base is calcium hydroxide. In one such embodiment, the addition of calcium hydroxide provides an aqueous solution having a $Ca(OH)_2$:glycine molar ratio of about 1.25:1 to about 1:1.

In another embodiment, a $ZrOCl_2$ solution is added to the pH adjusted aluminum-glycine solution. In one such embodiment, the molar ratio of Al:Zr is about 8. In another embodiment, the molar ratio of Al:Zr is about 7. In one other such embodiment, the molar ratio of Al:Zr is about 9.

For the above methods, the aluminum chloride salt may be obtained from a variety of sources. In one embodiment, the aluminum chloride salt includes aluminum trichloride, aluminum chlorohexahydrate and aluminum dichlorohydrate. In one such embodiment, the aluminum chloride salt is aluminum chlorohexahydrate.

The method can be used to make an antiperspirant active composition having a high SEC peak 4 in aqueous solution. In some embodiments, the antiperspirant active compositions obtained by this stepwise procedure include aluminum salts having an aluminum to chloride molar ratio of about 0.3:1 to about 3:1, the aluminum salt has a SEC Peak 4 to Peak 3 intensity ratio of at least 7 and a Peak 4 intensity greater than a Peak 5 intensity in aqueous solution.

The method can be used to make aluminum antiperspirant active compositions and/or aluminum-zirconium antiperspirant active compositions having high levels of low molecular weight Al and Zr species. The high levels of low molecular weight Al and Zr species is reflected in a SEC trace that has an intense Peak 4, low Peaks 1, 2, 3 and 5. The polymerization of the antiperspirant actives in aqueous solutions and the correspondent gelation process were followed by monitoring the molecular weight profile of the polyoxohalides in time by SEC. The relative retention time ("Kd") for each of these peaks varies depending on the experimental conditions, but the peaks remain relative to each other. Data for Tables in the examples was obtained using an SEC chromatogram using the following parameters: Waters®600 analytical pump and controller. Rheodyne® 77251 injector, Protein-Pak® 125 (Waters) column, Waters 2414 Refractive Index Detector. 5.56 mM nitric acid mobile phase. 0.50 ml/min flow rate. 2.0 microliter injection volume. Data was analyzed using Water® Empower software (Waters Corporation. Milford. Mass.). The concentration of the antiperspirant in solution does not affect the retention time in the machine.

The design of modern AP salts aims at actives with high levels of low molecular weight Al and Zr species, which is reflected in a SEC trace that has intense Peak 4 and low Peaks 1, 2, and 3. Throughout the present study, the levels of the species corresponding to these peaks are estimated based on the following ratios (or percentages):

$$f_{Pi} = \frac{Pi}{\Sigma Pj}$$

$$i = 1, 2, 3, 4, 5;$$

$$j = 2, 3, 4, 5$$

where $f_{Pi}$ is the fraction of peak i, and Pi or Pj are the intensity of peaks Pi or Pj, respectively. The amount of low molecular weight Al species will be correlated with the fraction, $f_{P4}$, or percentage, $f_{P4} \times 100$, of SEC-Peak 4. In brief, a preferred antiperspirant salt would have a very low $f_{P1}$, $f_{P2}$, $f_{P3}$, and/or $f_{P5}$, and a high $f_{P4}$.

In certain embodiments, the ratio of Peak 4 to Peak 3 is at least 8, 9, 10, 11, 12, 13, 14, 15, 16, 17, 18, 19, 20, 25, 30, 35, 40, 45, 50, 60, 70, 80, 90, 100, or any number up to infinity.

In one embodiment, an aluminum salt and/or aluminum-zirconium salt, in aqueous solution, exhibit a SEC profile wherein the SEC Peak 4 to Peak 3 intensity ratio is at least 7. In such embodiments, the percentage of SEC Peak 4 of a total area of Peaks 1, 2, 3, 4, 5, and 6 in the SEC chromatogram is: at least 50%; at least 60%; at least 70%; at least 80%; at least 90%, or 95 to 100%. In another such embodiment, the SEC Peak 4 area is 100%.

In another embodiment, the aluminum salt and/or the aluminum-zirconium salt, in aqueous solution, exhibits a SEC profile wherein the SEC Peak 4 to Peak 3 intensity ratio is at least 7 and exhibits low percentage of SEC Peak 3. In such embodiments, the composition has the percentage of SEC Peak 3 area of a total area of Peaks 1, 2, 3, 4, 5, and 6 in the SEC chromatogram is: less than about 10%; less than about 5%; less than about 2%; less than about 1%: less than about 0.9%: less than about 0.8%: less than about 0.7%: less than about 0.6%: of less than about 0.5%: less than about 0.4%; less than about 0.3%: less than about 0.2%: or less than about 0.1%. In another such embodiment, the composition has no SEC Peak 3 area.

In another embodiment, the aluminum salt and/or the aluminum-zirconium salt, in aqueous solution, exhibits a SEC profile wherein the SEC Peak 4 to Peak 3 intensity ratio is at least 7 and exhibits low percentages of SEC Peak 5. In such embodiments, the percentage of SEC Peak 5 area of a total area of Peaks 1, 2, 3, 4, 5, and 6 in the SEC chromatogram is: less than about 30%: less than about 20%; less than about 10%; less than about 5%; or less than about 1%. In another such embodiment, the composition has no SEC Peak 5 area.

In another embodiment, the aluminum salt and/or the aluminum-zirconium salt, in aqueous solution, exhibits a SEC profile wherein the SEC Peak 4 to Peak 3 ratio is at least 7, and exhibits a low percentage of SEC Peak 1 and a low percentage of SEC Peak 2. In such embodiment, the percentage of SEC Peak 1 area of a total area of Peaks 1, 2, 3, 4, 5, and 6 in the SEC chromatogram is: less than about 10%; a SEC Peak 1 area less than about 5%: less than about 2%; less than about 1%; less than about 0.9%: less than about 0.8%: of less than about 0.7%; less than about 0.6%: less than about 0.5%: less than about 0.4%: less than about 0.3%: less than about 0.2%; or less than about 0.1%. In another embodiment, the complex has no SEC Peak 1 area. In another embodiment, the percentage of SEC Peak 2 area of a total area of Peaks 1, 2, 3, 4, 5, and 6 in the SEC chromatogram is: less than about 10%: less than about 5%; less than about 2%; less than about 1%: less than about 0.9%; less than about 0.8%; less than about 0.7%; less than about 0.6%: less than about 0.5%; less than about 0.4%; less than about 0.3%; less than about 0.2%: or less than about 0.1%. In another embodiment, the composition has no SEC Peak 2 area.

The aluminum antiperspirant active compositions and/or aluminum-zirconium antiperspirant active compositions may be used in a variety of antiperspirant products. If the product is used as a solid powder, the size of the particles of antiperspirant active of the invention can be any desired size, and may include conventional sizes such as in the range of 2 to 100 microns, with selected grades having an average particle size of 30-40 microns: finer sized grades having an average particle size distribution of 2-10 microns with an average size of about 7 microns as made by a suitable dry-grinding method: and micronized grades having an average particle size of less than about or equal to 2 microns, or less than about or equal to 1.5 microns.

The compositions of this invention may be used to formulate antiperspirants having improved efficacy. Such antiperspirants include solids such as sticks and creams (creams sometimes being included in the term "soft solid"), gels, liquids (such as are suitable for roll-on products), and aerosols. The forms of these products may be suspensions or emulsions. These antiperspirant actives can be used as the antiperspirant active in any antiperspirant composition. Examples of formulations that can be made using the antiperspirant active and used of these compositions can be found in PCT/US2007/087145 (Published as WO2009/075678) and PCT/US2008/086556 (Published as WO2009/076591).

EXAMPLES

The invention is further described in the following examples. The examples are merely illustrative and do not in any way limit the scope of the invention as described and claimed.

Example 1

A 0.83M $AlCl_3.6H_2O$ (83 mmol) and 1.02 M glycine (102 mmol) is held at 95° C. in a glass reactor and stirred vigorously at 800 rpm using a Teflon stir bar. To this solution, a 2 N NaOH (204 mmol) is added dropwise over a 2 hour period. The reaction solution is left heated and stirring for an additional 1 hour. A molar ratio of $(OH)^-:(Al)^{3+}$ of 2.46 is employed. The pH after the reaction is 4.09.

Example 2

A 0.83M $AlCl_3.6H_2O$ (83 mmol) and 1.02 M glycine (102 mmol) is held at 95° C. in a glass reactor and stirred vigorously at 800 rpm using a Teflon stir bar. To this solution, a 2 N $Ca(OH)_2$ (102 mmol) is added dropwise over a 2 hour period. The reaction solution is left heated and stirring for an additional 1 hour. A molar ratio of $(OH)^-:(Al)^{3+}$ of 2.46 is employed. The pH after the reaction is 3.83.

Examples 3A to 3F

In this series of reactions, we attempt to quantify the inhibitory effects of $Ca(OH)_2$ on peak 3 formation. To this end, the basic source in each individual reaction is composed of a mixture of $Ca(OH)_2$ and NaOH. In an identical fashion to the previous two syntheses, a 0.83M $AlCl_3.6H_2O$ (83 mmol) and 1.02 M glycine (102 mmol) is held at 95° C. in a glass reactor and stirred vigorously at 800 rpm using a Teflon stir bar. To this solution, a 2N $Ca(OH)_2$/NaOH (mmol calculated to give $(OH)^-:(Al)^{3+}$ of 2.46) solution is added dropwise over a 2 hour period. The reaction solution is left heated and stirring for an additional 1 hour. The molar ratio of $(OH)^-:(Al)^{3+}$ is 2.46. The ratio ('/w) of $NaOH/Ca(OH)_2$ is shown below.

| Example | $\dfrac{NaOH (g)}{Ca(OH)_2 (g)}$ ratio |
|---|---|
| 3A | 1.1 |
| 3B | 3.2 |
| 3C | 4.9 |
| 3D | 5.6 |
| 3E | 6.4 |
| 3F | 7.6 |

Example 4

In the previous three experiments, the $NaOH/Ca(OH)_2$ basic source was added simultaneously to the a aluminum chloride solution. Here, the bases are added in succession. A 0.83M AlCl$_3$.6H$_2$O (83 mmol) and 1.02 M glycine (102 mmol) is held at 95° C. in a glass reactor and stirred vigorously at 800 rpm using a Teflon stir bar. To this solution, 2 N Ca(OH)$_2$ (16.46 mmol) is added dropwise over a 1 hour period. The reaction solution is left heated and stirring for 1 hour. 2NaOH (170.86 mmol) is added dropwise to the reaction flask over a 2 hour period. The reaction solution is left heated and stirring for an additional 1 hour. The final molar ratio of (OH)$^-$: (Al)$^{3+}$ is 2.46. The pH after the reaction is 4.09. The NaOH (g):Ca(OH)$_2$ (g) ratio is 5.6.

Example 5

In order to better understand the role of Ca$^{2+}$ in the reaction, this synthesis is performed by buffering the reaction flask with both Glycine and CaCl$_2$. NaOH is used as the sole basic source. A 0.83M AlO$_3$.6H$_2$O (83 mmol) is buffered with 1.02 M glycine (102 mmol) and 0.16M CaCl$_2$ (16.46 mmol) and held at 95° C. in a glass reactor while being stirred vigorously at 800 rpm using a Teflon stir bar. To this solution. 2 N NaOH (203.75 mmol) is added dropwise over a 2 hour period. The reaction solution is left heated and stirring for 1 hour. The final molar ratio of (OH)$^-$:(Al)$^{3+}$ is 2.46. The pH after the reaction is 3.87.

TABLE 1

Comparison of SEC Peak Distribution

| Example | Description | Al$^{3+}$/Ca$^{2+}$ | Relative Peak Distribution after reaction (%) | | | | Pk 4/Pk 3 |
| --- | --- | --- | --- | --- | --- | --- | --- |
| | | | Peak 2 | Peak 3 | Peak 4 | Peak 5 | |
| 1 | NaOH basic source | — | 0 | 61 | 28 | 11 | 0.46 |
| 2 | Ca(OH)$_2$ basic source | 0.55 | 0 | 0 | 93 | 7 | ∞ |
| 3A | NaOH/Ca(OH)$_2$ = 1.1 | 1.1 | 1 | 0 | 92 | 7 | ∞ |
| 3B | NaOH/Ca(OH)$_2$ = 3.2 | 2.2 | 0 | 1 | 92 | 7 | 92 |
| 3C | NaOH/Ca(OH)$_2$ = 4.9 | 3.0 | 0 | 2 | 93 | 5 | 46.5 |
| 3D | NaOH/Ca(OH)$_2$ = 5.6 | 3.4 | 0 | 3 | 92 | 5 | 30.6 |
| 5 | NaOH basic source. CaCl$_2$ buffer | 3.4 | 0 | 3 | 92 | 5 | 30.6 |
| 4 | NaOH/Ca(OH)$_2$ = 5.6, (successive addition) | 3.4 | 0 | 2 | 96 | 2 | 48 |
| 3E | NaOH/Ca(OH)$_2$ = 6.4 | 3.8 | 0 | 4 | 90 | 6 | 22.5 |
| 3F | NaOH/Ca(OH)$_2$ = 7.6 | 4.4 | 0 | 5 | 86 | 9 | 17.2 |

The syntheses described here show that Ca(OH)$_2$ can be partially substituted by NaOH with minimal effect on the SEC profile. Looking at Table 1, it is apparent that the amount of Ca$^{2+}$ used in the synthesis has a direct affect on the formation of peak 3. As the concentration of Ca$^{2+}$ is decreased, peak 3 species are formed in low concentration. Comparison of 3D and 5 shows that Ca(OH)$_2$ can be successfully replaced by a CaCl$_2$ buffer without any effect on the resulting profile. Comparison of 3D and 4 illustrates that adding the basic sources in succession leads to an increased peak 4 and decreased peak 3.

By providing a sufficient amount of Ca$^{2+}$ in the form of a base or a buffering salt, it is still possible to synthesis the high-efficacy aluminum chlorohydrate (ACH) antiperspirant active. In minimizing Ca(OH)$_2$ over NaOH ratio reaction (3A) to make a dominant ACH, the range of Ca salt in the final product, in which we keep percentage of Al in the EACH is equivalent to 12% of activated ACH, can be decreased by 1.88%.

What is claimed is:

1. A method of making an antiperspirant active composition comprising:
   I) heating an aqueous solution containing an aluminum salt having an aluminum to chloride molar ratio of about 0.3:1 to about 3:1, optionally with a buffer agent, at a temperature of about 50° C. to about 100° C. to reflux for a period of time of about 1 hour to about 6 hours to obtain an aluminum salt solution;
   II) adding an aqueous solution of sodium hydroxide to obtain an aluminum salt solution having an OH:Al molar ratio of about 2:1 to about 2.6:1 to obtain a pH adjusted aluminum salt solution having a pH of about 2 to about 5;
   III) providing a calcium ion to the solution; and
   IV) optionally adding an aqueous solution containing a zirconium compound to the pH adjusted aluminum salt solution to thereby obtain an aluminum-zirconium salt solution having a molar ratio of aluminum to zirconium of about 5:1 to about 10:1,
      wherein when the calcium ion source is a base, the weight ratio of sodium hydroxide to calcium base is greater than 0 to about 20; or when the calcium ion source is a salt, the weight ratio of sodium hydroxide to calcium ion is greater than 0 to about 11.

2. The method of claim 1, wherein the providing the calcium ion is adding calcium hydroxide to the aluminum salt solution.

3. The method of claim 2, wherein the providing the calcium ion is adding calcium hydroxide to the aluminum salt solution simultaneously with the sodium hydroxide solution.

4. The method of claim 2, wherein the providing the calcium ion is adding calcium hydroxide to the aluminum salt solution before the adding the sodium hydroxide.

5. The method of claim 2, wherein the providing the calcium ion is adding calcium hydroxide to the aluminum salt solution after the adding the sodium hydroxide.

6. The method of claim 1, wherein the providing the calcium ion is including a calcium salt in the aluminum salt solution.

7. The method of claim 6, wherein the calcium salt is calcium chloride.

8. The method of claim 1, wherein the buffer is present in a molar ratio of buffer to aluminum is about 0.1:1 to about 3:1.

9. The method of claim 1, wherein the aluminum chloride compound is chosen from aluminum trichloride, aluminum chlorohexahydrate, and aluminum dichlorohydrate.

10. The method of claim 1, wherein the composition further comprises the zirconium.

11. The method of claim 1, wherein the antiperspirant active composition exhibits a Size Exclusion Chromatography (SEC) chromatogram having a SEC Peak 4 to Peak 3 intensity ratio of at least 7 and a Peak 4 intensity greater than a Peak 5 intensity in aqueous solution.

12. The method of claim 11, wherein the antiperspirant active composition has a SEC Peak 4 area of at least 50% of a total area of Peaks 1, 2, 3, 4, 5, and 6 in the SEC chromatogram.

13. The method of claim 11, wherein the antiperspirant active composition has a SEC Peak 4 area of 95 to 100% of the total area of Peaks 1, 2, 3, 4, 5, and 6 in the SEC chromatogram.

14. The method of claim 11, wherein the antiperspirant active composition has a SEC Peak 3 area of less than about 10% of the total area of Peaks 1, 2, 3, 4, 5, and 6 in the SEC chromatogram.

15. The method of claim 11, wherein the antiperspirant active composition has no SEC Peak 3 area.

16. The method of claim 11, wherein the antiperspirant active composition has a SEC Peak 5 area of less than about 30% of the total area of Peaks 1, 2, 3, 4, 5, and 6.

17. The method of claim 11, wherein the antiperspirant active composition has no SEC Peak 5 area.

18. The method of claim 11, wherein the antiperspirant active composition has a SEC Peak 1 area of less than about 10% and a SEC Peak 2 area of less than about 10% of the total area of Peaks 1, 2, 3, 4, 5, and 6.

19. The method of claim 11, wherein the composition has a SEC Peak 4 area of 95 to 100%, no SEC Peak 3 area, and no SEC Peak 5 area of a total area of Peaks 1, 2, 3, 4, 5, and 6 in the SEC chromatogram.

20. The method of claim 1, wherein the calcium ion source is a calcium base, and the weight ratio of sodium hydroxide to calcium base is about 1 to about 8.

21. The method of claim 1, wherein the calcium ion source is a calcium base, and the weight ratio of sodium hydroxide to calcium base is one of 1.1, 3.2, 4.9, 5.6, 6.4, or 7.6.

22. The method of claim 1, wherein the calcium ion source is a calcium salt, and the weight ratio of sodium hydroxide to calcium ion is one of 1, 2, 3, 4, 5, 6, 7, 8, 9, 10, or 10.8.

* * * * *